United States Patent
Hoffmann et al.

(10) Patent No.: US 6,946,298 B2
(45) Date of Patent: Sep. 20, 2005

(54) KARL FISCHER REAGENT

(75) Inventors: Helga Hoffmann, Wonstorf (DE);
Katrin Schöffski, Hannover (DE)

(73) Assignee: Sigma-Aldrich Co., Highland, IL (US)

( * ) Notice: Subject to any disclaimer, the term of this patent is extended or adjusted under 35 U.S.C. 154(b) by 462 days.

(21) Appl. No.: 10/002,864

(22) Filed: Nov. 15, 2001

(65) Prior Publication Data

US 2002/0127726 A1 Sep. 12, 2002

(30) Foreign Application Priority Data

Nov. 15, 2000 (DE) .................................. DP 100 56 547

(51) Int. Cl.$^7$ ............................................. G01N 33/18
(52) U.S. Cl. ........................................................ 436/42
(58) Field of Search ........................................... 436/42

(56) References Cited

U.S. PATENT DOCUMENTS

| | | | | |
|---|---|---|---|---|
| 4,378,972 A | * | 4/1983 | Scholz ........................ | 436/42 |
| 4,851,352 A | * | 7/1989 | Fischer et al. ................ | 436/42 |
| 5,139,955 A | * | 8/1992 | Scholz ........................ | 205/788 |

FOREIGN PATENT DOCUMENTS

| DE | 19740965 | 3/1999 |
|---|---|---|
| EP | 0127740 | 12/1984 |

OTHER PUBLICATIONS

Sherman et al. Stoichometry and chemical metrology: Karl Fischer reagent; Accreditation and Quality Assurance, May 1999, v. 4, No. 6, pp. 230–234, Abstract and tecxt search from Google (see page link below).* http://www.springerlink.com/app/home/contribution.asp?wasp=d48072eewh4uvl493q7p&referrer=parent&backto=issue,6,16;journal,53,83;linkingpublicationresults,1:100393,1.*

Silke Grünke, Study of Side Reactions (thesis), Chemistry Department of the University of Hannover, 1999, Chapter 7, 132–145.

Eugen Scholz, Karl Fischer Titration Determination of Water, Springer–Verlag, 1984, vol. 20, 1–138.

* cited by examiner

*Primary Examiner*—Yelena G. Gakh
(74) *Attorney, Agent, or Firm*—Senniger Power

(57) ABSTRACT

A reagent for the determination of water content of a sample according to the Karl Fischer method is disclosed. The reagent comprises a base component comprised of a mixture of imidazole and a substituted imidazole. Preferably, the Karl Fischer reagent is a one component reagent comprising imidazole and 2-methylimidazole.

32 Claims, No Drawings

KARL FISCHER REAGENT

BACKGROUND OF THE INVENTION

The present invention relates to the Karl Fischer water determination method. More particularly, the present invention relates to a one-component Karl Fischer reagent comprising a base component comprising imidazole and a substituted imidazole.

The volumetric analysis of water was developed by Karl Fischer and is based on the oxidation of sulfur dioxide by iodine in the presence of water according to the following chemical equation:

$$2H_2O+SO_2+I_2 \leftrightarrows H_2SO_4+2HI$$

Typically, the Karl Fischer titration is performed in the presence of an alcohol as a solvent and a base, with the following chemical reaction presumed to occur:

$$H_2O+I_2+(RNH)SO_3R'+2RN \leftrightarrows (RNH)SO_4+2(RNH)I$$

wherein RN is a base and R' is alkyl (optionally substituted).

It is assumed that within the reagent an alkyl ester of sulfurous acid is formed from alcohol and sulfur dioxide. The latter is oxidized under consumption of stoichiometric amounts of water by iodine to the corresponding sulfuric acid alkyl ester. In practice, as alcohol components, mainly methanol and glycol monoalkyl ether are used. (See, E. Scholz "Karl Fischer-Titration," Springer Verlag 1984). The alcohol used not only serves as a solvent, but also participates in the reaction and hence influences the titration behavior of the reagents produced therewith. The end point titration can be recognized by an excess of iodine, which may be indicated visually, photometrically or electromagnetically, but a potentiometric recognition of the end point or by a dead-stop indication leads to substantially more thorough results.

There are four different basic forms of the titration according to Karl Fischer: (1) volumetric titration using a one component reagent; (2) volumetric titration with a two component reagent; (3) coulometric titration with a diaphragm; and (4) coulometric titration without a diaphragm. The four variants require different reagents.

For a one component titration, a reagent is necessary which keeps all reaction partners of water in one solution. For the latter purpose, sulfur dioxide, iodine, and the base are dissolved in an alcohol. In this solution, sulfur dioxide and the alcohol react with the base after being put together to form alkyl sulfite. The base accepts the released proton. When a water-containing sample is added to the component, the alkyl sulfite reacts with iodine and water to form alkyl sulfate and iodide. In the original reagent made by Karl Fischer, methanol was used as the alcoholic component. Later on, more stable reagents were yielded by using methyl glycol. In all one component reagents the titrimetric substance, i.e., the concentration of active iodine, decreases with time. As solvent for the sample in the titration beaker, most of the times methanol or a mixture of methanol and other solvent is used.

For a two component titration, two reagents are necessary. As titration component, a solution of iodine is methanol is used and a solution of sulfur dioxide and a base in methanol serves as the solvent. In the latter solvent, as in a one component reagent, alkyl sulfite is formed. The solvent component is placed in the titration beaker and subsequently titration is performed using the titration component. In contrast to the one component titration, in two component titration a decrease of the normality of the titration component does not occur, as long as no humidity penetrates into the holding flask.

The reagents used for the coulometric determination of water content according to Karl Fischer are different from those utilized in volumetric analysis. Instead of iodine, soluble iodide is used, from which during titration iodine is formed by anodic oxidation, which reacts in analogy to the above-described reaction scheme. The further constituents of the reagents are the same as in the volumetric reagents: sulfur dioxide, a base and an alcohol. In the case of the coulometric titration with diaphragm, the cathode and the anode space are separated by means of a diaphragm in the cell. Both spaces have to be filled up with reagent separately, with the cathode space usually being provided with a special cathode reagent. In the case of coulometric titration without a diaphragm, a separation of cathode and anode space is not necessary because the particular geometry of the cathode avoids the formation of substances that might be oxidized.

According to Karl Fischer, the base component of a reagent serves the function to neutralize the acid which is produced, and thereby facilitates a quantitative reaction. In former times, pyridine was used as a base in practice. Looking for toxicologically acceptable, non-harmful bases, EP-B-0 127 740 describes as further suitable bases imidazole, thiazole, pyrimidine, triazine or substitution products thereof. If imidazole was used in one component reagents, however, it was observed that upon longer storage times, especially at higher temperatures as occurring in hot countries, undesirable precipitations or crystals of imidazolium sulfate were formed, which led to problems in the flexible tube systems of the apparatus used for Karl Fischer determinations. Specifically, it was observed that because the plastic tubes of the Karl Fischer instruments were not completely gas tight, ambient air could enter the tubes. The ambient air contains a high amount of water vapor in hot, humid countries and the water can react with the iodine and methyl sulfite of the reagent to form methyl sulfate which can form a precipitate with the imidazolium ion. In order to prevent these precipitations, the Ph.D. thesis of Silke Grunke, Chemistry Department of the University of Hannover, 1999, Chapter 7, proposes to use a substituted imidazole, such as 2-methylimidazole in one component reagents instead of imidazole. However, when using this substituted imidazole, a rapid decay of normality is observed, leading to the situation that such one component reagents are not stable upon storage. The reason for this decay in normality appears directly related to the pH of the component solution. Because 2-methylimidazole is more basic than imidazole, the iodine present can form iodide and hypo iodide, which results in a significant decrease in available iodine and hence a reduction in normality.

Consequently, a need exists in the industry for an improved Karl Fischer reagent which is stable upon storage as a one component reagent regarding normality, and which, especially at high temperatures, does not tend to substantially precipitate.

SUMMARY OF THE INVENTION

The present invention relates to a reagent and methods for the determination of water content of a sample according to the Karl Fischer method wherein the reagent contains as its base component a mixture of imidazole and at least one substituted imidazole. In accordance with the present invention, preferred substituted imidazoles include 2-methylimidazole and 2-ethylimidazole. In a preferred embodiment of the present invention, a one component Karl Fischer volumetric analytical method is utilized.

Briefly, therefore, the present invention is directed to a reagent for the determination of water content of a sample according to the Karl Fischer method. The reagent comprises a base comprising imidazole and substituted imidazole having the general formula:

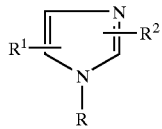

wherein R and $R^1$ are independently selected from the group consisting of hydrogen, phenyl, substituted phenyl, and a monovalent substituted or unsubstituted saturated or unsaturated hydrocarbyl moiety having from 1 to about 4 carbon atoms which may or may not be interrupted with hetero atoms, and $R^2$ is phenyl, substituted phenyl, a fused benzo ring, or a monovalent substituted or unsubstituted saturated or unsaturated hydrocarbyl moiety having from 1 to about 4 carbon atoms which may or may not be interrupted with hetero atoms.

The invention is further directed to a one component Karl Fischer reagent comprising from about 0.8 moles/Liter to about 1.3 moles/Liter imidazole, from about 0.6 moles/Liter to about 1 mole/Liter 2-methylimidazole, from about 0.1 moles/Liter to about 0.5 moles/Liter imidazole hydroiodide, from about 0.75 moles/Liter to about 1.6 moles/Liter sulfur dioxide, and from about 780 grams/Liter to about 820 grams/Liter diethylene glycol monethylether.

Other objects and features of this invention will be in part apparent and in part pointed out hereinafter.

DETAILED DESCRIPTION OF THE PREFERRED EMBODIMENTS

In accordance with the present invention, it has been discovered that a mixture of bases comprising imidazole and a substituted imidazole can be used as the base component of a Karl Fischer reagent. The substituted imidazole useful in the Karl Fischer reagents of the present invention have the following chemical formula:

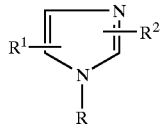

wherein R and $R^1$ are independently selected from the group consisting of hydrogen, phenyl, substituted phenyl, and a monovalent substituted or unsubstituted saturated or unsaturated hydrocarbyl moiety having from 1 to about 4 carbon atoms which may or may not be interrupted with hetero atoms, and $R^2$ is phenyl, substituted phenyl, a fused benzo ring, or a monovalent substituted or unsubstituted saturated or unsaturated hydrocarbyl moiety having from 1 to about 4 carbon atoms which may or may not be interrupted with hetero atoms. The hydrocarbyl moieties and phenyl group may optionally be substituted with, for example, halogen atoms such as chlorine, bromine, and fluorine. Also, the hydrocarbyl moiety may be interrupted with hetero atoms such as nitrogen, sulfur, and oxygen, for example.

Preferred substituted imidazoles for use in the present invention have 1, 2, or 3 saturated hydrocarbyl moieties having from 1 to about 4 carbon atoms or 1, 2, or 3, phenyl groups, substituted phenyl groups, or a fused benzo group. Examples of preferred substituted imidazoles useful in the present invention include benzimidazole, 1-methylimidazole, 1-ethylimidazole, 1-propylimidazole, 1-butylimidazole, 2-methylimidazole, 2-ethylimidazole, 2-propylimidazole, 2-butylimidazole, 4-methylimidazole, 4-butylimidazole, N-methylimidazole, 1,2-dimethylimidzazole, 1,2,4-trimethylimidazole, 1-phenylimidazole, 2-phenylimidazole, and mixtures and combinations thereof. Highly preferred substituted imidazoles include 2-methylimidazole, 2-ethylimidazole, or a mixture thereof, with 2-methylimidazole being most preferred as it is least harmful to health.

The substituted imidazoles described herein and used in combination with imidazole may be present in the Karl Fischer reagent as a single component (i.e., one substituted imidazole compound), or as one or more substituted imidazoles, or may be present with an additional base or bases. Other additional bases which can be included along with imidazole and a substituted imidazole(s) in the base component of a Karl Fischer reagent and which are known in the art include, for example, pyridine, diethanol amine, dipyridyl propane, lithium benzoate, alkyl benzoates or benzoates of organic bases such as, for example, imidazolium benzoate or methylimidazolium benzoate. Other bases known in the art are also suitable for use in the present invention.

For the base component of the Karl Fischer reagents described herein, it is preferred that the molar ratio of imidazole to substituted imidazole be from about 0.3:2 to about 2:0.3, more preferably from about 0.5:1.5 to about 1.5:0.5, and most preferably from about 1:1.3 to about 1.3:1. Similarly, if additional bases such as pyridine or diethanol amine, for example, are utilized in the base component of the Karl Fischer reagent in addition to the imidazole and substituted imidazole, it is preferred that the molar ratio of imidazole to the total amount of additional bases (that is, bases other than imidazole or the substituted imidazole(s)) be from about 0.3:2 to about 2:0.3, more preferably from about 0.5:1.5 to about 1.5:0.5, and most preferably from about 1:1.3 to about 1.3:1. Regardless of whether only imidazole and a substituted imidazole(s) are used as the base component or whether imidazole, a substituted imidazole(s) and additional bases are used as the base component of the Karl Fischer reagent, it is also preferred that the bases be used in such a combination that the resulting pH of the Karl Fischer reagent be from about 5.5 to about 8. Further, the total amount of all bases comprising the Karl Fischer reagent (that is, imidazole, substituted imidazole(s), and additional bases) is typically no more than about 10 moles/Liter, and preferably no more than about 3 moles/Liter, to ensure sufficient solubility of the bases into the solvent. The total amount of all bases also is typically at least about 0.3 moles/Liter, and preferably at least about 0.9 moles/Liter.

In addition to the base component described above, the Karl Fischer reagent described herein typically contains at least the common constituents found in a Karl Fischer reagent; in particular a solvent, sulfur dioxide and iodine or iodide. As a solvent for the reagent described herein, it is useful to employ a substantially water free alcohol, preferably an ethylene glycol monoalkylether with a lower alkyl group, preferably containing from 1 to about 5 carbon atoms, especially a diethylene glycol monoalkylether with a lower alkyl group, preferably with 1 to about 5 carbon atoms. Also, a propylene glycol monoalkylether with a lower alkyl group, preferably with 1 to about 5 carbon atoms can be utilized. A combination of two or more of the above-described substantially water free alcohols can also be used as the solvent in accordance with the present invention. Particularly preferred substantially water free alcohols include ethylene glycol monoalkylethers such as diethylene glycol monoethylether (DEGEE) and propylene glycol monoalkylethers as discussed in DE-A 197 40 965, which is hereby incorporated by reference. Other substantially water free alcohols such as methanol, propanol, 2-methoxyethanol and tetrahydrofurfaryl alcohol can also be used as the substantially water free alcohol component in accordance with the present invention. Typically, the alcohol component of the Karl Fischer reagent described herein is used in an amount of from about 30% by weight to about 80% by weight and preferably from about 50% by weight to about 70% by weight of the entire weight of the Karl Fischer reagent.

As mentioned above, the Karl Fischer reagent of the present invention contains sulfur dioxide. Typically, the molar ratio of the total amount of base, including the imidazole, the substituted imidazole(s) and additional bases (if any) to the sulfur dioxide is from about 10:1 to about 0.3:1, preferably from about 2:1 to about 0.5:1.

Preferably the Karl Fischer reagent of the present invention is a one component Karl Fischer reagent which comprises imidazole and a substituted imidazole, sulfur dioxide, iodine and substantially water free alcohol solvent. Typically, the amounts of the critical components in a one component Karl Fischer can be from about 0.2 moles/Liter to about 3 moles/Liter sulfur dioxide, from about 0.2 moles/Liter to about 6 moles/Liter total base, and from about 0.05 moles/Liter to about 1 moles/Liter iodine.

Along with the components of a one component Karl Fischer reagent as described above, a halic acid can optionally be included in the formulation. A halic acid can be added to the Karl Fischer reagent to buffer the reagent such that the pH of the reagent remains in the optimum range of from about 5.5 to about 8. Although other halic acids are acceptable for use with the Karl Fischer reagents of the present invention, a preferred halic acid is hydroiodic acid which forms imidazolium hydroiodide in the solution which allows the iodide ion to be present in the solution. Typically, the halic acid is added at a concentration of from about 0.1 moles/Liter to about 0.5 moles/Liter.

The Karl Fischer reagent of the present invention is typically manufactured by dissolving the imidazole and substituted imidazole (and any additional bases) base component, the sulfur dioxide, and the iodine in the solvent, optionally under cooling, to a temperature of from about 15° C. to about 50° C., preferably from about 20° C. to about 40° C. The amount of total base used typically is from 0.3 moles to about 10 moles, preferably from about 0.5 moles to about 5 moles, the amount of sulfur dioxide from about 0.1 moles to about 10 moles, preferably from about 0.5 moles to about 3 moles, the amount of iodine used from about 0.01 moles to about 3 moles, preferably from about 0.1 moles to about 1 mole, and the molar ratio of imidazole to substituted imidazole is typically from about 0.5:1 to about 1:0.5, with all values being related to 1 Liter of solution. The manufacture of the solution is completed in a usual manner under the exclusion of air humidity using purified starting materials.

For the water determination according to the Karl Fischer method the reagent according to the present invention are employed in a usual manner. In the titration cell, working medium, which may be a solvent or a reagent such as, for example methanol or the solvent component of the two component reagents, is placed. Subsequently, the prepared solution is titrated with the reagent according to the invention as a standard. Then, a sample, the water content of which has to be determined, is weighed and titrated in a usual manner.

Utilizing the reagent according to the present invention, the water content of solid and liquid samples can be determined. Numerous types of samples can be tested including, for example, salts, organic solvents, fats, oils, nutrients, and pharmaceutical preparations. Optionally, the reagents according to the invention may be combined with conventional Karl Fischer reagents.

A particularly preferred one component Karl Fischer reagent according to the present invention is comprised of from about 1 mole/Liter to about 1.3 moles/Liter imidazole, from about 0.8 moles/Liter to about 1.3 moles/Liter 2-methylimidazole, about 0.3 moles/Liter hydroiodic acid, from about 1.0 mole/Liter to about 1.3 moles/Liter sulfur dioxide and from about 0.08 moles/Liter to about 0.4 moles/Liter iodine, in one liter of diethylene glycol monoethylether.

Another particularly preferred one component Karl Fischer reagent according to the present invention is comprised of about 1.0 mole/Liter imidazole, about 1.0 mole/Liter 2-methylimidazole, 0.3 moles/Liter hydroiodic acid, about 1.0 mole/Liter sulfur dioxide, about 0.4 moles/Liter iodine and about 780 g/L diethylene glycol monoethylether.

Another particularly preferred one component Karl Fischer reagent according to the present invention is comprised of about 1.3 moles/Liter imidazole, about 0.7 moles/Liter 2-methylimidazole, about 0.2 moles/Liter hydroiodic acid, about 1.1 moles/Liter sulfur dioxide, about 0.2 moles/Liter iodine and about 820 g/L diethylene glycol monoethylether.

Another particularly preferred one component Karl Fischer reagent according to the present invention is comprised of about 0.90 moles/Liter imidazole, about 0.60 moles/Liter 2-methylimidazole, about 0.5 moles/Liter hydroiodic acid, about 0.75 moles/Liter sulfur dioxide, about 0.35 moles/Liter iodine, and about 820 g/L of diethylene glycol monoethylether.

Another particularly preferred one component Karl Fischer reagent according to the present invention is comprised of about 1.1 moles/Liter imidazole, about 1.0 mole/Liter 2-methylimidazole, about 0.1 moles/Liter hydroiodic acid, about 1.6 moles/Liter sulfur dioxide, about 0.15 moles/Liter iodine, and about 800 g/L diethylene glycol monoethylether.

The present invention also relates to the use of a mixture of imidazole and at least one substituted imidazole contained in a reagent for the determination of water according to the Karl Fischer method. In particular, this is a mixture of imidazole and at least one substituted imidazole as defined hereinabove. In a particularly preferred embodiment, a mixture of imidazole and at least one substituted imidazole is used in a one component Karl Fischer reagent. Additionally, the invention relates to a one component reagent for the determination of water according to the Karl Fischer method containing a mixture of imidazole and at least one substituted imidazole as defined herein, sulfur dioxide, iodine and a substantially water free alcohol.

The one component Karl Fischer reagent incorporating imidazole and a substituted imidazole, sulfur dioxide, iodine, and a substantially water free alcohol such as diethylene glycol monoethylether, is characterized by high storage stability, especially at high temperatures, which, for example, can occur in hot countries. The storage stability is evaluated with respect to the normality and the homogeneity of the reagent. Crystal formation within the reagent makes the latter useless because the flexible tubes of the titration apparatus may clog if crystals are present. A strong decease in normality makes the reagent useless because the velocity of titration decreases and the amount of reagent used becomes too high. A particular advantage of the reagent according to the invention is the fact that substantially no crystal formation occurs in the reagent, whereas normality merely shows a low decrease upon longer storage periods.

The present invention is illustrated by the following example which is merely for the purpose of illustration and is not to be regarded as limiting the scope of the invention or manner in which it may be practiced.

EXAMPLE 1

The following one component Karl Fischer reagents were prepared and analyzed for storage stability. Both crystal formation and decrease in normality were determined as a function of time.

| 1. Comparative reagent 1 (containing imidazole) | |
|---|---|
| Imidazole | 2.0 moles/Liter |
| Imidazole hydroiodide | 0.3 moles/Liter |
| Sulfur dioxide | 1.0 mole/Liter |
| Iodine | 0.4 moles/Liter |
| Diethylene glycol monoethylether | 800 grams |
| 2. Comparative reagent 2 (containing 2-methylimidazole) | |
| 2-methylimidazole | 2.0 moles/Liter |
| 2-methylimidazole hydroiodide | 0.3 moles/Liter |
| Sulfur dioxide | 1.0 mole/Liter |
| Iodine | 0.4 moles/Liter |
| Diethylene glycol monoethylether | 760 grams |
| 3. Comparative reagent 3 (containing ethylimidazole) | |
| 2-ethylimidazole | 2.0 moles/Liter |
| 2-methylimidazole hydroiodide | 0.3 moles/Liter |
| Sulfur dioxide | 1.0 mole/Liter |
| Iodine | 0.4 moles/Liter |
| Diethylene glycol monoethylether | 720 grams |
| 4. Reagent 4 according to the present invention (containing imidazole and 2-methylimidazole) | |
| Imidazole | 1.0 mole/Liter |
| 2-methylimidazole | 1.0 mole/Liter |
| Imidazole hydroiodide | 0.3 moles/Liter |
| Sulfur dioxide | 1.0 mole/Liter |
| Iodine | 0.4 moles/Liter |
| Diethylene glycol monoethylether | 760 grams |
| 5. Reagent 5 according to the present invention (containing imidazole/2-ethylimidazole) | |
| Imidazole | 1.0 mole/Liter |
| 2-ethylimidazole | 1.0 mole/Liter |
| 2-ethylimidazole hydroiodide | 0.3 moles/Liter |
| Sulfur dioxide | 1.0 mole/Liter |
| Iodine | 0.4 moles/Liter |
| Diethylene glycol monoethylether | 780 grams |

Crystal Formation of Reagents: 50 mL of each reagent was mixed with 0.2 mL of water and stored at room temperature.

Stability of Titration Compound (methanol as working medium)

| Decrease in Normality | Reagent 1 | Reagent 2 | Reagent 3 | Reagent 4 | Reagent 5 |
|---|---|---|---|---|---|
| After 1 week | 0.40% | 1.97% | 0.60% | 0.40% | 0.38% |
| After 4 weeks | 1.09% | 2.99% | 1.79% | 1.55% | 1.46% |
| After 4 months | 6.3% | 23.9% | 21.3% | 9.6% | 10.1% |

Reagent 1 shows very good stability but in the presence of humidity it forms crystals very rapidly. Once crystals for in the reagent, it cannot effectively be used due to apparatus clogging problems.

Reagents 2 and 3 did not show any crystal formation in the presence of humidity. Reagents 2 and 3 did, however, show a high decrease in normality of more than 20% of the original normality after four months. Once the normality decrease reaches this level, the reagents are virtually unuseable.

In contrast to the shortcomings of Reagents 1, 2, and 3, Reagents 4 and 5 did not show any crystal formation and showed good normality stability. This indicates that Reagents 4 and 5, which were prepared according to the present invention utilizing imidazole and a substituted imidazole, show optimum properties.

In view of the above, it will be seen that the several objects of the invention are achieved. As various changes could be made in the above-described Karl Fischer reagents without departing from the scope of the invention, it is intended that all matter contained in the above description be interpreted as illustrative and not in a limiting sense.

What is claimed is:

1. A one component Karl Fischer reagent having increased stability and homogeneity comprising iodine and a base comprising imidazole and a substituted imidazole, wherein the substituted imidazole is selected from the group consisting of 2-methylimidazole, 2-ethylimidazole, 2-propylimidazole, 2-butylimidazole, 1,2-dimethylimidazole, 1,2,4-trimethylimidazole, and 2-phenylimidazole;
   wherein the molar ratio of imidazole to substituted imidazole is from about 0.5:1.5 to about 1.5:0.5; and
   wherein the reagent is suitable for use as a one component reagent in volumetric Karl Fischer titrations.

2. The reagent as set forth in claim 1 wherein the substituted imidazole is selected from the group consisting of 2-methylimidazole, 2-ethylimidazole and a combination thereof.

3. The reagent as set forth in claim 1 wherein the molar ratio of imidazole to substituted imidazole is from about 1:1.3 to about 1.3:1.

4. The reagent as set forth in claim 1 further comprising a substantially water free alcohol solvent.

5. The reagent as set forth in claim 4 wherein the alcohol solvent is an ethylene glycol monoalkylether.

Crystal Formation

| Homogeneity | Reagent 1 | Reagent 2 | Reagent 3 | Reagent 4 | Reagent 5 |
|---|---|---|---|---|---|
| After 1 week | Few Crystals | No Crystals | No Crystals | No Crystals | No Crystals |
| After 3 weeks | Many Crystals | No Crystals | No Crystals | No Crystals | No Crystals |
| After 3 months | Many Crystals | No Crystals | No Crystals | No Crystals | No Crystals |

6. The reagent as set forth in claim 5 wherein the ethylene glycol monoalkylether comprises an alkyl group having from 1 to about 5 carbon atoms.

7. The reagent as set forth in claim 4 wherein the alcohol solvent is a diethylene glycol monoalkylether.

8. The reagent as set forth in claim 7 wherein the diethylene glycol monoalkylether comprises an alkyl group having from 1 to about 5 carbon atoms.

9. The reagent as set forth in claim 4 wherein the alcohol solvent is a propylene glycol monoalkylether.

10. The reagent as set forth in claim 9 wherein the propylene glycol monoalkylether comprises an alkyl group having from 1 to about 5 carbon atoms.

11. The reagent as set forth in claim 4 wherein the alcohol solvent is selected from the group consisting of ethylene glycol monoalkylethers, diethylene glycol monoethylether, propylene glycol monoalkylethers, methanol, propanol, 2-methoxyethanol, tetrahydrofurfuryl alcohol, and mixtures thereof.

12. The reagent as set forth in claim 4 wherein the alcohol solvent is diethylene glycol monoethylether.

13. The reagent as set forth in claim 4 wherein the alcohol solvent is present in a proportion from about 30% by weight to about 80% by weight based on the weight of the reagent.

14. The reagent as set forth in claim 13 wherein the alcohol solvent is present in a proportion from about 50% by weight to about 70% by weight based on the weight of the reagent.

15. The reagent as set forth in claim 4 further comprising sulfur dioxide.

16. The reagent as set forth in claim 15 further comprising a halic acid.

17. The reagent as set forth in claim 16 wherein the concentration of the halic acid is from about 0.1 moles/Liter to about 0.5 moles/Liter.

18. The reagent as set forth in claim 16 wherein the halic acid is hydroiodic acid.

19. The reagent as set forth in claim 16 further comprising a base selected from the group consisting of pyridine, diethanol amine, dipyridyl propane, imidazolium benzoate, methylimidazolium benzoate, and combinations thereof.

20. The reagent as set forth in claim 19 wherein the molar ratio of imidazole to additional base is from about 0.3:2 to about 2:0.3.

21. The reagent as set forth in claim 19 wherein the molar ratio of imidazole to additional base is from about 0.5:1.5 to about 1.5:0.5.

22. The reagent as set forth in claim 19 wherein the molar ratio of imidazole to additional base is from about 1:1.3 to about 1.3:1.

23. The reagent as set forth in claim 19 wherein the total amount of base in the reagent is no more than about 10 moles/Liter.

24. The reagent as set forth in claim 19 wherein the total amount of base in the reagent is no more than about 3 moles/Liter.

25. The reagent as set forth in claim 19 wherein the pH of the reagent is from about 5.5 to about 8.

26. The reagent as set forth in claim 19 wherein the reagent comprises from about 0.1 moles/Liter to about 10 moles/Liter total base, from about 0.1 moles/Liter to about 10 moles/Liter sulfur dioxide, and from about 0.01 moles/Liter to about 3 moles/Liter iodine.

27. The reagent as set forth in claim 19 wherein the reagent comprises from about 0.5 moles/Liter to about 5 moles/Liter total base, from about 0.5 moles/Liter to about 3 moles/Liter sulfur dioxide, and from about 0.1 moles/Liter to about 1 mole/Liter iodine.

28. The reagent as set forth in claim 19 wherein the molar ratio of the base to the sulfur dioxide is from about 10:1 to about 0.3:1.

29. The reagent as set forth in claim 19 wherein the molar ratio of the base to the sulfur dioxide is from about 2:1 to about 0.5:1.

30. The reagent as set forth in claim 15 wherein the pH of the reagent is from about 5.5 to about 8.

31. A one component Karl Fischer reagent comprising iodine and from about 0.8 moles/Liter to about 1.3 moles/Liters imidazole, from about 0.6 moles/Liter to about 1 mole/Liter 2-methylimidazole, from about 0.1 moles/Liter to about 0.5 moles/Liter imidazole hydroiodide, from about 0.75 moles/Liter to about 1.6 moles/Liter sulfur dioxide, and from about 780 grams/Liter to about 820 grams/Liter diethylene glycol monoethylether and wherein the reagent is suitable for use as a one component reagent in volumetric Karl Fischer titrations.

32. The one component Karl Fischer reagent as set forth in claim 31 wherein the pH of the reagent is from about 5.5 to about 8.

* * * * *